United States Patent

Kubela et al.

[11] 4,048,314
[45] Sept. 13, 1977

[54] MORPHOLINO CONTAINING 4-ARYLPIPERIDINE DERIVATIVES

[75] Inventors: Rudolph Kubela, Cote St. Luc, Canada; Jose Maria Do Nascimento, Moscavide, Portugal

[73] Assignee: Delmar Chemicals Limited, Ville la Salle, Canada

[21] Appl. No.: 533,642

[22] Filed: Dec. 17, 1974

[51] Int. Cl.$^2$ .......................................... C07D 413/04
[52] U.S. Cl. .......................... 424/248.55; 424/248.5;
424/248.56; 424/267; 260/247.1 M; 260/247.2
B; 260/247.5 G; 260/293.55; 260/293.64;
260/293.71; 260/293.73; 260/293.75;
260/293.77; 260/293.78; 260/293.81;
260/243.3; 544/129; 544/130
[58] Field of Search ............... 260/247.2 B, 247.5 G;
424/248, 248.55, 248.56

[56] References Cited

U.S. PATENT DOCUMENTS

| | | | |
|---|---|---|---|
| 3,125,574 | 3/1964 | Janssen | 260/247.5 G |
| 3,158,616 | 11/1964 | Adickes et al. | 260/293.73 |

Primary Examiner—Henry R. Jiles
Assistant Examiner—R. W. Ramsuer
Attorney, Agent, or Firm—Virgil H. Marsh

[57] ABSTRACT

The present invention is concerned with novel 4-aryl-3/4-amino/hydroxy-piperidine derivatives of the general formula I:

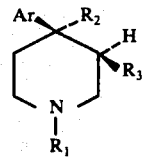

wherein $R_1$ represents hydrogen; lower alkyl; lower aralkyl; lower acyl; aminoalkyl, wherein the alkyl moiety contains 2 to 6 carbon atoms and the amino moiety may be mono- or dialkyl substituted —$(CH_2)_n$—COOH; —$(CH_2)_n$—OH;

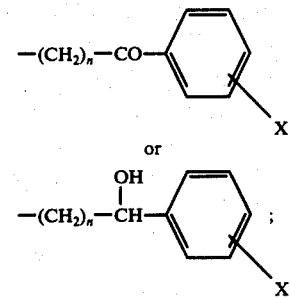

wherein X is hydrogen or halogen and $n$ is 1, 2, 3 or 4; one of $R_2$ and $R_3$ represents a cyano, or a free amino group or a derivative thereof and the other represents a free or protected hydroxyl group; or $R_2$ represents an azido group when $R_3$ represents a free or protected hydroxyl group, or $R_2$ and $R_3$ together with their associated ring carbons represent an oxazepine ring, and Ar represents an aryl group which may be substituted by lower alkyl, lower alkoxy, halogen or $CF_3$, as well as addition salts thereof with organic or inorganic acids.

Compounds of formula I generally have useful biological properties and in particular, some such compounds had been found to exhibit inter alia, significant antidepressant activity. Illustrative of compounds of formula I is 1-methyl-4-phenyl-4-acetoxy-3-(4-piperidinyl)piperidine. The present invention also provides processes for the production of, and pharmaceutical compositions containing the novel compounds of formula I.

4 Claims, No Drawings

MORPHOLINO CONTAINING 4-ARYLPIPERIDINE DERIVATIVES

The present invention relates to novel 4-arylpiperidine derivatives, processes for the production thereof and compositions containing same.

DETAILED DESCRIPTION OF THE INVENTION

According to one aspect of the present invention there is provided novel 4-aryl-3/4-amino/hydroxy-piperidine derivatives of the general formula I:

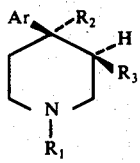

wherein $R_1$ represents hydrogen; lower alkyl; lower aralkyl; lower acyl; aminoalkyl, wherein the alkyl moiety contains 2 to 6 carbon atoms and the amino moiety may be mono- or dialkyl substituted $-(CH_2)_n-COOH$; $-(CH_2)_n-OH$;

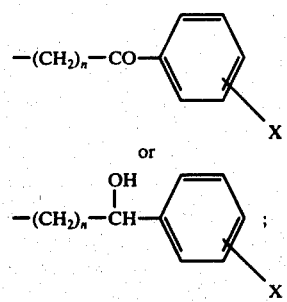

wherein X is hydrogen or halogen and $n$ is 1, 2, 3 or 4; one of $R_2$ and $R_3$ represents a cyano, or a free amino group or a derivative thereof and the other represents a free or protected hydroxyl group; or $R_2$ represents an azido group when $R_3$ represents a free or protected hydroxyl group, or $R_2$ and $R_3$ together with their associated ring carbons represent an oxazepine ring, and Ar represents an aryl group which may be substituted by lower alkyl, lower alkoxy, halogen or $CF_3$, as well as addition salts thereof with organic or inorganic acids.

Since the compounds of formula I have chiral centres at $C_3$ and $C_4$, it will be obvious to one skilled in the art that these compounds may be present as stereoisomers and optical isomers. The connotation of the general formulae presented herein is to include all such isomers either separated or in $d,l$ mixtures.

Also, it will be noted that substituent groups $R_2$ and $R_3$ are always trans to each other in the compounds of formula I.

Throughout this specification the terms "lower alkyl" and "lower acyl" refer to alkyl and acyl groups having at most six, and preferably at most four, carbon atoms. Examples of lower alkyl groups include methyl, ethyl, isopropyl, propyl, butyl, isobutyl sec. and tert. butyl, pentyl, isopentyl, neopentyl and the various hexyl isomers. Lower acyl groups include acetyl, propionyl, etc, and aminoalkyl includes aminoethyl, aminopropyl, aminobutyl, aminopentyl and aminohexyl. The terms lower aralkyl refers to such groups having at most six, preferably at most four, carbon atoms in the alkyl moiety, examples thereof being phenyl-lower-alkyl such as benzyl, phenethyl and napthyllower-alkyl such as 2-naphthyl-methyl. Aryl group Ar may be phenyl and 1- or 2-naphthyl, but preferably phenyl, which may be substituted with chlorine, bromine or fluorine as halogen.

Amino group $R_2$ or $R_3$ may be of the formula:

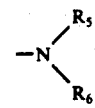

wherein $R_5$ and $R_6$ individually represent hydrogen; lower alkyl optionally substituted with a hydroxyl group or an ester moiety of formula —COOlower alkyl; lower aralkyl, the lower alkylene moiety of which may carry a hydroxyl group; or adamantyl; or together with the nitrogen and optionally, an oxygen atom, represent a 5- or 6-membered heterocyclic ring. Preferred heterocyclic rings represented by

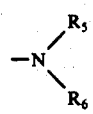

are pyrrolidine, piperidine and morpholine. Specific amine derivatives contemplated by the present invention include those having:

| | |
|---|---|
| amide moieties of formula | $-NH-\overset{O}{\underset{\|\|}{C}}R$; |
| sulphonamide moieties of formula | $-NH-SO_2R^1$; and |
| urea moieties of formula | $-NH-CO-NHR^1$; | wherein R is lower alkyl and $R^1$ is lower alkyl or aryl, especially phenyl, which may be substituted by lower alkyl. Examples of protected hydroxyl groups $R_2$ or $R_3$ are the corresponding esters of formula

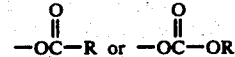

and ethers of formula O—R, where R is a lower alkyl group. A restricted class of compounds of formula I are those of formula III:

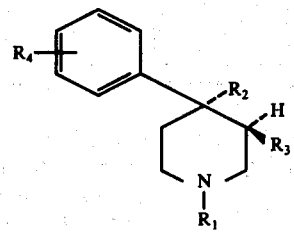

wherein $R_1$ is lower alkyl or acyl; one of $R_2$ and $R_3$ is the amino group $-NR_5R_6$ defined above and the other is hydroxyl or an ester group of formula

where
R is a lower alkyl group, and
$R_4$ is hydrogen, lower alkyl, lower alkoxy, halogen or $CF_3$ but preferably hydrogen or lower alkyl.

The present invention in a further aspect, provides processes for producing compounds of formula I. In one process, the novel compounds of the present invention may be prepared from an epoxide of formula IV:

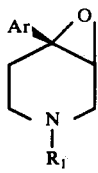

wherein $R_1$ and Ar are as defined above for formula I.

The compounds of formula IV are converted into the compounds of formula I by a reaction involving cleavage of the epoxide ring. This is effected according to one process of the present invention by reaction with ammonia; an azide; a cyanide; or a primary or secondary amine, the cleaving agent being chosen to provide the desired groups $R_2$ and $R_3$ in the compound of formula I.

The amine cleaving agent may be of the formula:

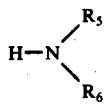

wherein $R_5$ and $R_6$ are as defined above.

The azide or cyanide used may be an alkali metal azide or cyanide, such as sodium or potassium azide and sodium or potassium cyanide.

As will be appreciated, compounds of formula IV wherein $R_1$ is hydrogen are secondary amines and in certain instances may be involved in undesirable competing reactions involving cleavage of the epoxide ring with the selected cleaving agent. This is only likely to occur to any significant extent when the cleaving agent is bulky in nature, and the possibility of said undesirable reactions occurring may be reduced by effecting the reaction at a lower temperature than in the other instances, for example, a temperature below 100° C compared with a temperature of between 100°-200° C, usually about 150° C. However, in such cases, it is preferred to produce the desired compounds of formula I wherein $R_1$ is hydrogen by cleaving the epoxide ring of a corresponding compound of formula I wherein $R_1$ is an amine protecting group, such as acyl, with the desired cleaving agent and subsequently convert group $R_1$ to hydrogen in known manner, for example, by hydrolysis with acid or base.

Moreover, compounds of formula I may in general be used as intermediates in the obtention of other compounds of formula I. For example, those compounds of formula I wherein $R_1$ is alkyl or acyl, may be obtained from the compound of formula I wherein $R_1$ is hydrogen by simple alkylation or acylation by known standard procedures using, for example, alkylhalides or acyl halides. Compounds of formula I wherein $R_2$ is a free amino group may be obtained by reduction in a known manner, for example, using a complex metal hydride of the corresponding azide, and substituted amines and amine derivatives may be obtained from the corresponding free amino compounds by, for example, alkylation using alkyl halides or by reaction with acyl halides (to form amide derivatives) sulphonyl halides (to form sulphonamide derivatives) and isocyanates (to form ureas). Alternatively, some derivatives may, if desired, be prepared directly from the epoxy compound. For example, the epoxide ring in the compound of formula IV may be cleaved with an amide derivative, such as a toluene sulphonamide in the form of an alkali metal salt, such as the sodium or potassium salt, resulting in the direct formation of a toluene sulphonamide amine derivative of formula I. Likewise, compounds of formula I wherein $R_2$ or $R_3$ is a protected hydroxyl group may be obtained from the corresponding free hydroxyl compound, for example, by esterification or etherification in known manner.

As it will be readily appreciated, formula I above includes inter alia two series of amino-alcohol structural isomers, namely, those of formula Ia and Ib below:

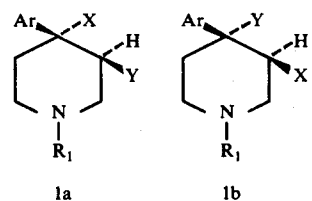

Ia  Ib wherein $R_1$ and Ar are as defined broadly above and X is $R_2$ or $R_3$ when a free or protected hydroxyl group, and Y is $R_2$ or $R_3$ when cyano, or a free amino or a derivative thereof.

Also, included within formula I are compounds of formula Ib above, but wherein Y is azide.

Cleavage of the epoxide ring of the 3,4-epoxypiperidines of formula IV generally results in the production of both of such structural isomers but the relative amounts of each isomer varies depending to a small extent on the solvent, if present, in which the reaction is effected but also on the steric properties of the cleaving agent.

However, the overriding factor involved in determining the relative proportions of the two isomers is the steric properties, i.e., bulk, of the cleaving agent.

For example, if cleavage of the epoxide ring of the compound of formula IV is effected with an azide, only isomer Ib is obtained. The same isomer predominates to a large extent if a non-hindered amine, such as one of the formula $H_2NCH_2-R$ wherein R is, for example, alkyl phenyl, aralkyl, a typical example of such a compound being benzylamine, etc. is used. In all these cases, the nucleophilic attack is predominantly on the tertiary carbon atom of the piperidine ring.

If isomer Ib wherein Y is a free amino group is required, this is easily obtained by reduction of the corresponding azide by known procedures.

A cyanide or an amine of medium size or bulk such as pyrrolidine, dimethylamine and hydroxyethylmethylamine result in the formation of an approximately one to one mixture of the two possible isomers. In such cases, the tertiary and secondary carbon atoms in the piperidine ring are equally favoured as the site for attack by the nucleophilic reagent.

Finally, bulky amines such as amino-adamantane, morpholine piperidine and tertiary butylamine and, surprisingly, ammonia, for example, in the form of an aqueous solution, result in the predominance of the isomer of formula Ia, the favoured site of attack being the secondary carbon atom in the epoxide ring.

If the mixture of isomers obtained as the product in any specific reaction is not utilizable in that form due to the undesirable presence of one or more isomers, the isomers may be separated by standard techniques generally utilizing differences in the physical and/or chemical properties between the isomers, such as relative solubilities, differing recrystallization rates and differing retention rates in chromatographic separation processes, such as column chromatography.

The 4-arylpiperidines of formula I form acid addition salts with various inorganic or organic acids and such salts are included within the scope of the present invention. Of special interest are the pharmaceutically acceptable acid addition salts which are usually more convenient to handle than the free compounds of formula I. Acids which form such salts include hydrochloric acid, hydrobromic acid, sulfuric acid, phosphoric acid, nitric acid, acetic acid, maleic acid, fumaric acid, tartaric acid, succinic acid, citric acid, camphorsulfonic acid, ethanesulfonic acid, ascorbic acid and lactic acid.

Of the starting materials, namely, the 3,4-epoxypiperidines of formula IV:

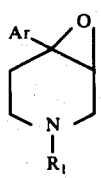

IV the compound wherein $R_1$ is methyl and Ar is phenyl is known being described in the literature along with its preparation. Other compounds of formula IV wherein Ar and $R_1$ are as defined above may be prepared in an analogous manner. For example, they may be obtained by the epoxidation of compounds of formula V:

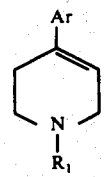

V wherein $R_1$ and Ar are as defined above.

The epoxidation may be effected in several ways for example:

1. oxidation using a percarboxylic acid according to the following scheme:

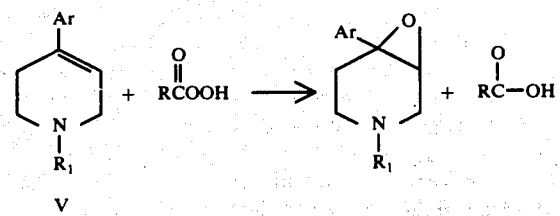

wherein $R_1$ is acyl and Ar are as defined above, or 2. from a halohydrin in the presence of a base according to the following scheme:

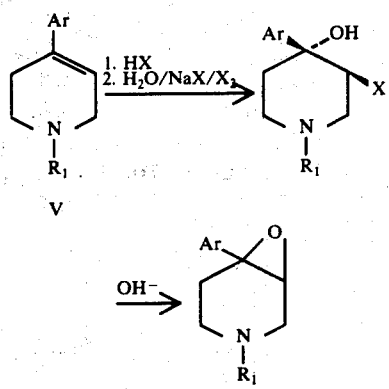

wherein $R_1$ is hydrogen, i.e., the nitrogen is basic in character, and X is halogen.

However, it will be obvious to the skilled chemist that the actual procedure used for the epoxidation must be chosen to avoid the possibility of undesirable side reactions. For example, when $R_1$ in formula V above is acyl, one cannot utilize the halohydrin route because of the detrimental effects of the reagents involved on the acyl group. In such cases the epoxidation may be effected using a percarboxylic acid or, alternatively, the epoxy compound where $R_1$ is hydrogen may be prepared using route 2 and this compound subsequently acylated by known procedures (as mentioned above) if desired.

It will be readily apparent that in general the said epoxy compounds where $R_1$ is other than hydrogen may be obtained from the corresponding epoxy compounds where $R_1$ is hydrogen by alkylation, acylation etc. in known manner of the latter compounds.

Some of the 4-aryl-1,2,3,6-tetrahydropyridines of formula V, namely, those of formula VI:

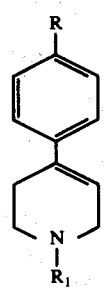

VI wherein R is hydrogen or methyl and $R_1$ is various hydrocarbon moieties are known compounds being described along with a process for their preparation, for example, in J.A.C.S. (1956) Vol. 78, p. 425–428. Any novel compounds of formula V may be prepared in a similar manner to the known compounds with, of course, the appropriate choice of starting materials.

An alternative process for preparing these compounds wherein Ar represents a phenyl group comprises reacting formaldehyde, an appropriately substituted α-methylstyrene and an amine according to the following scheme:

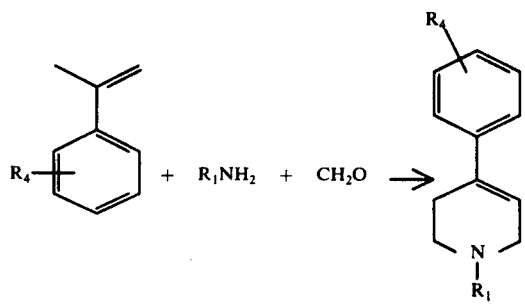

wherein $R_1$ and $R_4$ are as defined above, and amine $R_1NH_2$ is in the form of an acid addition salt.

Again compounds wherein substituent $R_1$ is hydrogen may be converted into compounds wherein $R_1$ is other than hydrogen by standard known procedures as described above.

The novel 4-arylpiperidines of the present invention possess useful biological properties and generally they have activity, as determined by standard tests, indicative of possible use as at least one of the following; intestinal relaxant, antihistamine, anticholinergic, uterine relaxant, local anesthetic, anticonvulsant and diuretic; for example, compounds of formula Ia when administered to mice have generally been found to have a significant stimulatory effect on the central nervous system indicative of ultimate antidepressant and similar clinical use in humans.

The following table summarizes the results obtained when some compounds of formula Ia above were evaluated for antidepressant activity using standard test procedures (ref. R. A. Turner, P. Hebborn, Screening Methods in Pharmacology, Vol. II, Acad. Pr., N.Y., London, 1971, page 214). Reserpine was used to induce ptosis and the test compounds were administered per os. The results obtained in the same test for the known antidepressant imipramine are included as a comparison. Response values >3 are considered pharmacologically significant.

| COMPOUND | DOSE mg/kg | RESPONSE |
|---|---|---|
| 1-methyl-4-phenyl-4-hydroxy-3-(4-morpholino)piperidine | 25 | 6 |
| | 10 | 5 |
| 1-methyl-4-phenyl-4-hydroxy-3-(N-adamantylamino)piperidine | 25 | 5 |
| | 10 | 5 |
| 1-methyl-4-phenyl-4-propionyloxy-3-(4-morpholino)piperidine | 25 | 9 |
| | 10 | 6 |
| | 5 | 5 |
| 1-methyl-4-phenyl-4-hydroxy-3-(4-pyrrolidinyl)piperidine | 25 | 7 |
| | 10 | 5 |
| 1-methyl-4-phenyl-4-acetoxy-3-(4-pyrrolidinyl)piperidine | 25 | 9 |
| | 10 | 7 |
| | 5 | 6 |
| 1-methyl-4-phenyl-4-acetoxy-3-(4-piperidinyl)piperazine | 10 | 9 |
| | 5 | 9 |
| | 2.5 | 5 |
| 1-methyl-4-phenyl-4-hydroxy-3-[(2'-hydroxyethylmethyl)amino]piperidine | 25 | 5 |
| Imipramine | 25 | 4 |
| | 5 | 1 |

It can be seen that the antidepressant activity of the compounds of the present invention compares very favourably with the known drug imipramine and for that reason these compounds constitute a preferred class within the generic formula I.

Compounds of formula Ib, such as 1-methyl-4-phenyl-4-benzylamino-3-hydroxy piperidine, have been shown to have, inter alia, local anesthetic and antiarrhythmic activity.

The present invention further provides in another of its aspects a pharmaceutical composition comprising as an essential active ingredient at least one active compound of formula I or a pharmaceutically acceptable acid addition salt thereof in association with a pharmaceutically acceptable carrier therefor.

The compositions of the present invention are preferably administered orally, rectally or parenterally. Advantageously, the composition is in a dosage unit form appropriate to the desired mode of administration. For example, the dosage unit may be a tablet, capsule, pill, powder, packet, granule, wafer, elixir, suppository, or a measured quantity of a suspension, solution, a syrup or segregated multiples of the foregoing. The term "dosage units form" as used in the specification and claims refers to physically discrete units suitable as unitary dosages for human subjects and animals, each unit containing a predetermined quantity of active material calculated to produce the desired therapeutic effect in admixture, or otherwise in association, with a pharmaceutical carrier, the quantity of the active ingredient being such that one or more units are normally required for a single therapeutic administration or that, in the case of severable units such as scored tablets, at least one fraction such as a half or a quarter of a severable unit is required for a single therapeutic administration.

Usually the compositions of this invention contain the active ingredient in an amount of at least 0.5% by weight based on the total weight of the composition and not more than 95% by weight. Conveniently, the compositions of the invention when in dosage unit form contain 0.5 mg. to 100 mg., and more conveniently from 5 mg. to 50 mg., of the active ingredient of Formula I.

The compositions of the present invention will normally consist of at least one compound of formula I, advantageously a compound of formula III, and more advantageously a compound from the preferred groups defined by formula Ia, or a pharmaceutically acceptable acid addition salt thereof, admixed with a carrier, or diluted by a carrier, or enclosed or encapsulated by a carrier in the form of a capsule, sachet, catchet, paper or other container. A carrier which serves as a vehicle, excipient or diluent medium for the therapeutically active ingredient may be a solid, semi-solid or a sterile liquid.

Some examples of the carriers which may be employed in the pharmaceutical compositions of the invention are lactose, dextrose, sorbitol, mannitol, starches such as wheat, corn, or potato starch, gum acacia, calcium phosphate, liquid paraffin, coca butter, oil of theobroma, alginates, tragacanth, gelatin, syrup B.P., methyl cellulose, polyoxethylene sorbitan monolaurate, and methyl and propyl hydroxybenzoates. The choice of carrier is determined by the preferred form of administration the solubility of the compound and standard pharmaceutical practice, all as more clearly set forth in "Remington's Practice of Pharmacy" by E. W. Martin and E. F. Cook, a well-known reference work in this field. In the case of tablets, a lubricant may be incorporated to prevent sticking and binding of the powdered ingredients in the dies and on the punch of the tabletting machine. For such purpose, there may be employed, for example, talc, aluminum, magnesium or calcium stearates or polyethylene glycols "Carbowaxes" (Registered Trade Mark) of suitable molecular weight.

The pharmaceutical compositions of this invention may contain, in addition to the active 4-arylpiperidine ingredient, one or more other physiologically active ingredients which elicit desirable complementary effects.

Examples of suitable pharmaceutical compositions according to the present invention are presented below for the purposes of facilitating a better understanding of this aspect of the invention.

COMPOSITIONS

Composition 1

For oral administration, sugar coated tablets may have the following composition, the tablets being made up in the usual manner.

| Ingredient | Amount (mg) |
| --- | --- |
| 1-methyl-4-phenyl-4-hydroxy-3-(N-aminoadamantyl)piperidine | 25 |
| Lactose | 60 |
| Starch | 50 |
| Sugar | 75 |
| Talc | 5 |
| Gum Arabic | 5 |

Composition 2

Capsules, made up in the usual manner may have the following composition:

| Ingredient | Amount (mg) |
| --- | --- |
| 1-methyl-4-phenyl-4-hydroxy-3-(4-morpholinyl)piperidine | 5 |
| Lactose | 145 |

It will be appreciated that the above specific compounds may be replaced by other active compounds of the present invention, such as 1-methyl-4-phenyl-4-acetoxy-3-pyrrolidinylpiperidine.

As indicated hereinbefore, it has been found in accordance with the present invention that the compounds of Formula I possess useful biological properties in that such compounds possess the inherent applied use characteristics of exerting for example, antidepressants on the central nervous system. Compounds possessing such activity may have very valuable therapeutic utility as potential medicaments in the form of pharmaceutical compositions in eliciting advantageous central nervous system effects when administered to humans and animals. Accordingly, central nervous system effects, on humans and animals, may be elicited by administering a therapeutically effective dose of one or more of the active compounds of Formula I (preferably a compound of Formula III, and more preferably a compound of Formula Ia) wherein CNS symptom being treated, the age, health and weight of the recipient, the extent of the symptom, kind of concurrent treatment, if any, and the precise nature of the effect desired. In practise, based upon standard pharmacological animal studies, particularly in mice, it has been found that the administration of doses of 1 to 100 mg. of the active compounds of this invention per kg. of animal body weight will usually elicit the aforementioned CNS effect(s) normally without producing any marked side effects.

The present invention will be further described with reference to, but not limited by, the following specific examples.

EXAMPLE 1

1-Methyl-4-phenyl-4-hydroxy-3-(1-piperidyl)piperidine and its hydrochloride

A mixture of 2.81 g. of 1-methyl-4-phenyl-3,4-epoxypiperidine and 1.5 g. of piperidine in 10 ml of ethylene glycol was heated at 150° C. in an oil bath overnight (18 hours). The reaction mixture was then cooled, 5 ml. of water added and then extracted three times with an equal volume of methylene chloride on each occasion. The organic fractions so obtained were washed with a saturated solution of sodium chloride, dried over anhydrous sodium sulfate, filtered and finally evaporated in vacuo to give 3.61 g. of crude 1-methyl-4-phenyl-4-hydroxy-3-(1-piperidyl) piperidine in the form of a resinous residue which was dissolved in ethyl acetate and filtered through a layer of silica gel.

This compound was then converted to its monohydrochloride by forming a solution in methanol, adding one equivalent of N HCl and evaporating the resulting solution to dryness in vacuo. Further portions of ethanol were added to the residue and the resulting solution in each case was evaporated to dryness. The final residue, which was the desired hydrochloride, when recrystallized from acetone had a melting point of 241°-2° C. The free base was found to be pure by t.l.c. chromatography, by infrared spectroscopy and NMR. The structure of the hydrochloride was confirmed by NMR spectroscopy and elemental analysis. Elemental analysis of the hydrochloride salt was found to be as follows:

|  | C | H | N | Cl |
| --- | --- | --- | --- | --- |
| Calc. | 65.68 | 8.76 | 9.01 | 11.41 |
| Found | 65.48 | 8.57 | 8.72 | 11.62 |

EXAMPLE 2

1-Methyl-4-phenyl-4-acetoxy-3-(1-piperidyl)piperidine and its hydrochloride

A solution comprising 0.9 g. of 1-methyl-4-phenyl-4-hydroxy-3-(1piperidyl)piperidine hydrochloride in 10 ml. of water was basified with sodium carbonate, extracted with methylene chloride and the organic fraction evaporated in vacuo. To the residue was added 2 ml. of pyridine and 1 ml. of acetic anhydride and the resulting solution left for one hour at ambient temperature. A portion of water was then added to the solution and, after stirring the combined solution for one hour, it was again basified with sodium carbonate, extracted with methylene chloride and evaporated to dryness to yield 0.50 g. of the desired free base product. The free base was converted into its hydrochloride by the method described in Example 1 and the resulting 1-methyl-4-phenyl-4-acetoxy-3-(1-piperidyl)piperidine hydrochloride had a melting point of 177°-8° C.

The product was found pure by t.l.c. and the structure confirmed by infrared and N.M.R. spectroscopy.

EXAMPLE 3

1-Methyl-4-phenyl-4-hydroxy-3-(4-morpholinyl)piperidine and its hydrochloride

A mixture of 2.7 g. of 1-methyl-4-phenyl-3,4-epoxypiperidine and 1.5 g. of morpholine in solution in 3 ml. of ethylene glycol was heated at 150° C. in an oil bath three hours. The reaction mixture was then cooled and 5 ml. of water added whereupon 2.84 g. of the desired free base was obtained in crystalline form. An analytical sample obtained by recrystallization from acetone-ether had a melting point of 154°-6° C.

Using the method described in Example 1, 1-methyl-4-phenyl-4-hydroxy-3-(4-morpholinyl)piperidine hydrochloride was prepared and found to have a melting point of 239°-40° C.

Elementary analysis:

|  | C | H | N | Cl |
|---|---|---|---|---|
| Calc. | 61.42 | 8.06 | 8.96 | 11.35 |
| Found | 61.11 | 8.37 | 8.85 | 11.85 |

EXAMPLE 4

1-Methyl-4-phenyl-4-acetoxy-3-(4-morpholinyl)piperidine and its hydrochloride 1.5 G. of 1-methyl-4-phenyl-4-hydroxy-3-(4-morpholinyl) piperidine was dissolved in 3 ml. of acetic anhydride containing 0.1 ml. of $BF_3$ etherate and the resulting solution refluxed for 5 minutes. After cooling ice was added to the reaction mixture which was then stirred for one hour. Basification with sodium carbonate resulted in the precipitation of 1.6 g. of the desired 1-methyl-4-phenyl-4-acetoxy-3-(4-morpholinyl) piperidine in crystalline form. Recrystallization from methanol gave a sample having a melting point of 119°-20° C.

Using the method described in Example 1 the corresponding hydrochloride was obtained and this has a melting point of 186°-7° C.

EXAMPLE 5

1-Methyl-4-phenyl-4-propoxy-3-(4-morpholinyl)piperidine and its hydrochloride

A solution comprising 1.5 g. of 1-methyl-4-phenyl-4-hydroxy-3-(4-morpholinyl)piperidine and 0.1 ml. of $BF_3$ etherate 48% complex in 2 ml. of propionic anhydride was refluxed for five minutes. After cooling ice was added and the solution left overnight. The solution was then basified with sodium carbonate, extracted three times with methylene chloride, dried with sodium sulfate, filtered, and, finally, evaporated to dryness. The oily residue obtained in 1.6 g. yield was shown by IR and NMR spectra to be the desired 1-methyl-4-phenyl-4-propioxy-3-(4-morpholinyl)piperidine.

Using the method described in Example 1 the free base was converted into the corresponding hydrochloride which was recrystallized from methanol in the form of crystals having a melting point of 135°-7° C.

EXAMPLE 6

1-Methyl-4-phenyl-4-hydroxy-3-(N-adamantylamino)-piperidine and its hydrochloride A mixture of 1.5 g. of 1-methyl-4-phenyl-3,4-epoxypiperidine and 1.5 g. of aminoadamantane in 5 ml. of ethylene glycol was heated at 150° C. on an oil bath overnight. The reaction mixture was cooled, 5 ml. of water added with a precipitate formed. The reaction mixture was extracted with methylene chloride three times. The organic fractions so obtained were washed with sodium chloride, dried over sodium sulfate, filtered and finally evaporated to give 2.83 g. of the desired 1-methyl-4-phenyl-4-hydroxy-3-(N-aminoadamantyl)piperidine which, when crystallized partially from hexane, had a melting point of 92°-94° C.

Using the method described in Example 1 the free base was converted into its hydrochloride which was found to have a melting point of 220°-2° C.

EXAMPLE 7 a.

1-Methyl-4-phenyl-4-(1-pyrrolidinyl)-3-hydroxypiperidine

A mixture of 3.8 g. of 1-methyl-4-phenyl-3,4-epoxypiperidine and 1.6 g. of pyrrolidine in 4 ml. of ethylene glycol was heated overnight at 150° C. After cooling the resulting solution was treated as described in Example 1 and 4.6 g. of residue were obtained. This residue was dissolved in acetone and upon standing 0.81 g. of a crystalline material having a melting point of 149°-51° C. was obtained. Use of T.L.C. and IR and NMR spectrography indicated that the compound was pure and that it was 1-methyl-4-phenyl-4-(1-pyrrolidinyl)-3-hydroxy piperidine.

b.

1-Methyl-4-phenyl-4-hydroxy-3-(1-pyrrolidinyl)piperidine and its hydrochloride

The mother liquor obtained from Part (a) above, subsequent to the removal of the crystalline precipitate, was evaporated to dryness to give a product which was shown by IR and NMR spectra to be 1-methyl-4-phenyl-4-hydroxy-3-(1-pyrrolidinyl)piperidine which after several recrystallizations had a melting point of 110° C.

Using the method described in Example 1 the free base was converted into the corresponding hydrochloride whose structure was confirmed by IR spectra and whose melting point after several recrystallizations was found to be 186°-8° C.

EXAMPLE 8

1-Methyl-4-phenyl-4-(N-benzylamino)-3-hydroxy piperidine and its hydrochloride

A mixture comprising 3.7 g. of 1-methyl-4-phenyl-3,4-epoxypiperidine, 2.5 g. of benzylamine and 10 ml. of ethylene glycol was heated at 150° C. on an oil bath overnight. After work-up by the method described in Example 1, 5.45 g. of residue were obtained from which 4.11 g. of the desired free base 1-methyl-4-phenyl-4-(N-benzylamino)-3-hydroxy piperidine were isolated, this compound having a melting point of 162°-4° C.

Using the method described in Example 1 the free base was converted into the corresponding hydrochloride which was found to have a melting point of 191°-3° C.

The structure of both these compounds were confirmed by IR and NMR spectroscopy and elemental analysis which for the free base was as follows:

Elementary analysis:

| | C: | H: | | N: | |
|---|---|---|---|---|---|
| Calc. | C: | H: | 8.16 | N: | 9.45 |
| Found | C: | H: | 7.96 | N: | 9.61 |

EXAMPLE 9

1-Methyl-4-phenyl-4-azido-3-hydroxypiperidine 1.4 G. of sodium azide ($NaN_3$) in 6 ml. of water was added to a solution of 3.6 g. of 1-methyl-4-phenyl-3,4-epoxypiperidine in 20 ml. of dioxane and the resulting combined solution refluxed for 2 hours. A further portion of 1.4 g. of $NaN_3$ in 6 ml. of water was then added and the reaction mixture refluxed overnight. Upon cooling 3.2 g. of crystals of the desired 1-methyl-4-phenyl-4-azido-3-hydroxypiperidine were obtained, which had a melting point of 170°–71° C.

The structure of this compound was confirmed by IR and NMR spectroscopy and elemental analysis and its relationship with the derivatives as described in succeeding examples 10 to 13.

Elementary analysis:

|       | C     | H    | N     |
|-------|-------|------|-------|
| Calc. | 62.05 | 6.96 | 24.12 |
| Found | 62.02 | 7.19 | 23.87 |

EXAMPLE 10

1-Methyl-4-phenyl-4-amino-3-hydroxypiperidine and its hydrochloride 0.95 G. of 1-methyl-4-phenyl-4-azido-3-hydroxypiperidine were added to a solution of 0.7 g. of lithium aluminium hydride in 50 ml. of ether and the reaction mixture gently refluxed for 6 hours. Ethyl acetate was then added to destroy the excess lithium aluminum hydride and water added slowly until no more precipitate was formed. The resulting slurry was extracted several times with methylene chloride. The methylene chloride solution after drying with sodium sulfate, was filtered and evaporated to dryness to give 0.43 g. of a crystalline residue which was shown by IR and NMR spectroscopy to be 1-methyl-4-phenyl-4-amino-3-hydroxy piperidine having a melting point of 148°–9° C.

Elementary analysis:

|       | H    | N     |
|-------|------|-------|
| Calc. | 8.79 | 13.58 |
| Found | 9.13 | 13.67 |

Using the method described in Example 1 the free base was converted into the corresponding hydrochloride which was found to have a melting point of 176°–8° C.

EXAMPLE 11

1-Methyl-4-phenyl-4-amino-3-hydroxypiperidine

A solution comprising 2 g. of 1-methyl-4-phenyl-4-azido-3-hydroxypiperidine in 20 ml. of methanol was hydrogenated for 12 hours at 30 p.s.i. in the presence of 100 mg. of a catalyst comprising 5% palladium on carbon. The catalyst was removed by filtration and the residual solution evaporated to dryness to give 1.8 g. of the desired 1-methyl-4-phenyl-4-amino-3-hydroxypiperidine which was shown by IR spectra etc. to be identical with the product of example 10.

EXAMPLE 12

1-Methyl-4-phenyl-4-N-benzylidenimino-3-hydroxypiperidine 160 mg. of benzaldehyde was added to 2.8 g. of 1-methyl-4phenyl-4-amino-3-hydroxypiperidine dissolved in 5 ml. of methanol. A crystalline precipitate began to form after 10 minutes and precipitation was complete after one hour. The crystals so formed were removed by filtration and shown by analysis to be the desired 1-methyl-4-phenyl-4-N-benzylidenimino-3-hydroxypiperidine which had a melting point of 187°–9° C.

EXAMPLE 13

1-Methyl-4-phenyl-4-N-benzylamino-3-hydroxypiperidine 1.4 G. of 1-methyl-4-phenyl-4-N-benzylidenimino-3-hydroxypiperidine were added to a solution of 0.7 g. of lithium aluminium hydride in 50 ml. of tetrahydrofuran and the resulting mixture gently refluxed for 3 hours. Addition of ethyl acetate destroyed the excess lithium aluminium hydride and water was then added slowly until no more precipitation was formed. The resulting slurry was extracted several times in methylene chloride and the organic fractions were dried with sodium sulfate, filtered and evaporated to give crystals of a substance which by melting point and IR spectra was shown to be identical with the compound described in Example 8, i.e., 1-methyl-4-phenyl-4-N-benzylamino-3-hydroxypiperidine.

EXAMPLE 14

Trans-pyrido[3,4-b]-7-methyl-4-oxo-perhydro-9a-phenyl-1,5-oxazepine 0.5 G. of freshly distilled methylacrylate were added to a solution of 1 g. of 1-methyl-4-phenyl-4-amino-3-hydroxypiperidine in 5 ml. of methanol and the resulting solution allowed to stand for two days at ambient temperatures. Upon evaporation of the solution 1.4 g. of a drystalline product having a melting point of 148°–50° C. were obtained and this was shown by IR and NMR spectroscopy and and elemental analysis to be the desired trans-pyrido [3,4-b]-7-methyl-4-oxo-perhydro-9a-phenyl-1,5-oxazepine.

EXAMPLE 15

1-Methyl-4-phenyl-4-cyano-3-hydroxy-piperidine and its hydrochloride

A mixture of 1.9 g. of 1-methyl-4-phenyl-3,4-epoxypiperidine, 600 mg. of NaCN and 5 ml. of ethylene glycol was heated at 120° C. overnight in an oil bath. The resulting solution was cooled to produce 0.78 g. of product which, after being removed by filtration, was recrystallized from methanol. The desired product had a m.p. of 215°–8° C. Reaction with hydrochloric acid in the usual manner gave the corresponding hydrochloride salt which had a m.p. of 238°–40° C.

EXAMPLE 16

1-Methyl-4-phenyl-4-cyano-3-acetoxypiperidine and its hydrochloride 1.5 G. of 1-methyl-4-phenyl-4-cyano-3-hydroxypiperidine was dissolved in a mixture of 2 ml. of piperidine and 2 ml. acetic anhydride, the resulting mixture being left at room temperature for 1 hour. A portion of water was then added to the reaction mixture which was then stirred for a further hour. A work-up procedure as described in Example 4 was used to obtain 0.8 g. of the desired 1-methyl-4-phenyl-4-cyano-3-acetoxypiperidine. Reaction with hydrochloric acid in the usual manner gave the corresponding hydrochloride salt which was found to have a m.p. of 243°–50° C.

EXAMPLE 17

1-Methyl-3-amino-4-hydroxy-4-phenyl piperidine and its hydrochloride 1.9 G. of 1-methyl-4-phenyl-3,4-epoxy piperidine was stirred in 20 ml. of concentrated aqueous ammonia and the mixture heated for 18 hours in a pressurized vessel (oil bath temperature 120°–40° C). After cooling the ammonia solution was evaporated to dryness. The residue was recrystallized from acetone to give 1.2 g. of the desired product having a m.p. of 136°–8° C.

The free base was converted in the usual manner into its hydrochloride, the salt having a m.p. of 186°–8° C.

Elementary analysis:

|       | C     | H    | N     | Cl    |
|-------|-------|------|-------|-------|
| Calc. | 59.37 | 7.89 | 11.54 | 14.60 |
| Found | 59.26 | 8.03 | 11.15 | 14.40 |

EXAMPLE 18

1-Methyl-4-hydroxy-4-phenyl-3-(N'-phenylcarbamido) piperidine

500 Mg. of 1-methyl-3-amino-4-hydroxy-4-phenyl piperidine was dissolved in 5 ml. of methylenechloride and 260 mg. of phenylisocyanate was added to the mixture at room temperature. After 15 minutes of stirring the reaction was complete as indicated by t.l.c. The solvent was removed in vacuo, the residue dissolved in ethanol and 2 ml. of 1 N hydrochloric acid added. The solvents were evaporated in vacuo to dryness and the residue recrystallized from ether - acetone. 750 Mg. of the desired crystalline product was obtained, which after one recrystallisation, had a melting point of 223°–5° C.

EXAMPLE 19

1-Methyl-4-hydroxy-4-phenyl-3-(N-p-toluenesulfonamido)piperidine and its hydrochloride A mixture comprising 1.9 g. of 1-methyl-4-phenyl-3,4-epoxypiperidine, 4 ml. of ethyleneglycol and 2.0 g. of potassium salt of p-toluenesulfonamide was stirred at 130° C. for 18 hours. The solvent was partially removed in vacuo, the residue diluted with $H_2O$ and then extracted into methylene chloride. After evaporation of the solvent 1.2 g. of solid residue comprising the desired product remained. This was converted in the usual manner into the corresponding hydrochloride salt which had a melting point of 255°–8° C.

EXAMPLE 20

1-Acetyl-3,4-epoxy-4-phenylpiperidine 6.0 G. of 85% m-chloroperbenzoic acid was added portionwise to a solution of 5.8 g. of 1-acetyl-4-phenyl-1,2,5,6-tetrahydropyridine dissolved in 100 ml. of methylene chloride, the latter being cooled during the addition using an ice bath. The mixture was stirred 18 hours at room temperature, then washed with water, sodium bisulfite solution, sodium carbonate solution and, finally, again with water. After evaporation 4.8 g. of solid remained, which was recrystallised from ether to give 3.9 g. of the desired product which was found to have a melting point of 68°–71° C.

EXAMPLE 21

1-Acetyl-3-dimethylamino-4-hydroxy-4-phenylpiperidine and its hydrochloride 2.95 G. of 1-acetyl-4-phenyl-3,4-epoxypiperidine dissolved in 50 ml. of ethanol was saturated with gaseous dimethylamine. The mixture was heated for 18 hours at 90° C. in a pressurized vessel. After evaporation of the solvent 3.2 g. of resin which remained was crystallised twice from ether to give 1.9 g. of the desired 1-acetyl-3-dimethylamino-4-hydroxy-4-phenylpiperidine which melted at 118°–9° C.

This product was converted in the usual manner into the corresponding hydrochloride salt having a melting point of 230° C. dec.

EXAMPLE 22

1-Ethyl-4-phenyl-4-hydroxy-3-(4-morpholinyl)piperidine and its hydrochloride A mixture formed by adding 1.9 g. (50 m mol.) of lithium aluminium hydride to a solution of 1-acetyl-4-phenyl-4-hydroxy-3-(4-morpholinyl)piperidine in 50 ml. of dry tetrahydrofuran was refluxed for 3 hours. The reaction mixture was cooled and excess lithium aluminium hydride destroyed by the careful addition of ethyl acetate. The solution was diluted with 5 ml. of water treated with 5 ml. of 10% sodium hydride and finally sufficient water to produce a granular precipitate which was removed by filtration and washed with methylene chloride. The filtrate was further diluted with water and the resulting mixture extracted with methylene chloride. The combined organic extracts were dried over sodium sulphate and evaporated to dryness whereby 2.5 g. of the desired product was obtained in an impure form. The so-obtained free base was treated in the usual manner with one equivalent of hydrochloric acid in ethanol followed by evaporation to dryness to give the corresponding monohydrochloride in a crude form. Recrystallization of the crude product from acetone gave the desired monohydrochloride as a pink solid having a melting point of 186°–187° C.

EXAMPLE 23

1-Ethyl-4-phenyl-4-acetoxy-3-(4-morpholinyl)piperidine and its hydrochloride A solution comprising 1.0 g. of 1-ethyl-4-phenyl-4-hydroxy-3-(4-morpholinyl)piperidine, 5 ml. acetic anhydride and 5 drops of borontrifluoride etherate was refluxed for one hour. The reaction mixture was cooled in an ice bath and 10 ml. of water added. The cooled aqueous solution was then adjusted to pH 9 with 10% sodium carbonate solution and extracted with methylene chloride, the organic fraction subsequently being dried over sodium sulphate. Concentration in vacuo of the dried solution gave 1.2 g. of crude 1-ethyl-4-phenyl-4-acetoxy-3-(4-morpholinyl)piperidine and its hydrochloride as a dark oil. The crude product was purified by column chromatography using a silica gel column and methylene chloride as eluent whereupon 0.73 g. of pure product was obtained in the form of an oil which solidified on standing.

The free base was converted to its corresponding monohydrochloride having a melting point of 147°–8° C. by treating an ethanolic solution thereof with an equivalent of hydrochloric acid.

EXAMPLE 24

1-Methyl-4-p-tolyl-4-hydroxy-3-(4-morpholinyl)piperidine and its hydrochloride A solution comprising 5 g. 1-methyl-4-(4-tolyl-3,4-epoxypiperidine, 5 g. morpholine and 5 ml. ethylene glycol was heated at 150° C. on an oil bath for 3 hours. The resulting solution was cooled, diluted with water and extracted with methylene chloride. The organic fraction was dried over sodium sulphate and evaporated in vacuo to give 6.55 g. of crude product as a brown solid. Purification involving suspending the crude product in cyclohexane gave 3.25 g. of the desired 1-methyl-4-p-tolyl-4-hydroxy-3-(4-morpholinyl)piperidine as a creamy crystalline product having a melting point of 128°-31° C.

The so-obtained free base was converted into its monochloride having a melting point of 137° C. (dec.) by treating an isopropanol solution thereof with one equivalent of hydrochloric acid.

The starting 1-methyl-4-p-tolyl-3,4-epoxypiperidine was prepared as follows:

52 Ml. of a 10% sodium hydroxide solution was added dropwise to a stirred solution of 22.08 g. of the corresponding bromohydrin hydrochloride in 500 ml. water, the solution being cooled in an ice bath during the addition. After the addition was complete the reaction mixture was stirred at room temperature for 30 minutes. The resulting solution was saturated with potassium carbonate resulting in the formation of a precipitate which was removed by filtration. The precipitate was washed with water and dried at room temperature thereby providing 12.6 g. of the desired 1-methyl-4-tolyl-3,4-epoxypiperidine as a white solid having a melting point of 55°-7° C.

EXAMPLE 25

1-Methyl-4-p-tolyl-4-acetoxy-3-(4-morpholinyl)piperidine and its hydrochloride A solution of 1.3 g. of 1-methyl-4-tolyl-4-hydroxy-3-(4-morpholinyl)piperidine in 3 ml. of acetic anhydride was heated at 120° C for 30 minutes. The solution was cooled, diluted with water and the pH adjusted to 7 with sodium bicarbonate. The resulting solution was extracted with methylene chloride and the organic phase dried over sodium sulphate. Concentration in vacuo gave the crude acetate product as a dark oil. Filtration of an ethyl acetate solution of the crude product through silica gel gave 1.2 g. of the pure desired free base as a solid.

The free base was converted into the corresponding monohydrochloride in the usual manner, the hydrochloride having a melting point of 174° C. upon being recrystallized from isopropanol.

The compounds included in the following Tables were prepared using the procedures of the foregoing Examples with the appropriate changes in reactants and where necessary, reaction conditions.

The compounds in Table 1 are all of formula III above wherein $R_1$ is methyl and $R_4$ is hydrogen.

Table 1

| Example | $R_2$ | $R_3$ | M.P. (° C) Base | M.P. (° C) HCl Salt |
|---|---|---|---|---|
| 26) | NH—CH$_2$—CH$_2$OH | —OH | — | 196–8 |
| 27) | —N(CH$_3$)—CH$_2$—CH$_2$OH | —OH | — | 210–2 |
| 28) | —OH | —N(CH$_3$)—CH$_2$—C$_6$H$_5$ | — | 183–5 |
| 29) | —N(CH$_3$)—CH$_2$—C$_6$H$_5$ | —OH | 160–2 | — |
| 30) | —OH | —N(CH$_3$)—CH(CH$_3$)—CH(OH)—C$_6$H$_5$ | — | 212–4 |
| 31) | —OH | —N(CH$_3$)—CH$_2$—CH$_2$OH | 193–6 | — |
| 32) | —OC(O)CH$_3$ | —N(pyrrolidinyl) | — | 163–4 |
| 33) | —OH | —N(piperidinyl) | — | 186–8 |
| 34) | —O—C(O)—CH$_2$CH$_3$ | —N(piperidinyl) | oil | — |
| 35) | —O—C(O)—CH$_3$ | —N(CH$_3$)—CH$_2$—C$_6$H$_5$ | — | 166–8 |
| 36) | —OH | —N(CH$_3$)$_2$ | — | 223–5 |

Table 1-continued

| Example | $R_2$ | $R_3$ | M.P. (° C) Base | M.P. (° C) HCl Salt |
|---|---|---|---|---|
| 37) | $-N(CH_3)_2$ | —OH | — | 114–16 dec. (approx.) |
| 38) | $-N(CH_3)_2$ | $-OC(=O)-CH_3$ | oil | — |
| 39) | $NHCH_3$ | —OH | — | 147–50 |
| 40) | —OH | $-NH-SO_2-C_6H_4-CH_3$ | — | 255–8 |
| 41) | —OH | $-NH-C(CH_3)_2-CH_3$ | — | 121–5 (very hydroscopic) |
| 42) | $-CO-CH_3$ | $-NH-C(CH_3)_2-CH_3$ | — | 214–6 |
| 43) | $-CO-CH_3$ | $-N(CH_3)_2$ | — | 161–3 dec. |
| 44) | —OH | $-NH-CH(CH_3)_2$ | — | Very hydroscopic (m.p. not measured) |
| 45) | $-OCO-CH_3$ | $-NH-CH(CH_3)_2$ | — | 191–2 |
| 46) | $-OCO-CH_3$ | $-NH-CH(Ph)_2$ | — | 107–9 |
| 47) | —OH | $-NH-CH(Ph)_2$ | — | 221–3 |
| 48) | —OH | $-N(CH_3)-CH_2-CH_3$ | — | 67–73 |
| 49) | $-OCOCH_3$ | $-N(CH_2-CH_3)_2$ | — | 160–2 |
| 50) | $-OCOCH_3$ | $-N(CH_3)(CH_2-CH_3)$ | — | 172–3 |
| 51) | —OH | $-NH-C(CH_3)_2-CH_2-OH$ | — | Maleate salt melting point 155–6 |
| 52) | —OH | $-N(CH_2-CH_2-OH)(CH_2-Ph)$ | — | 137–41 |
| 53) | —OH | $-NH-\overset{*}{C}H(CH_3)-CH_2-Ph$ | — | 158–62 |
| 54) | —OH | $-N(CH_2-CH_3)_2$ | — | 178–81 |
| 55) | —OH | $-NH-CH_2-CH_2-COOCH_3$ | — | 194–6 |
| 56) | —OH | $-NH-CO-NH-C_6H_5$ | — | 223–5 |
| 57) | $-OCOCH_3$ | $-NH-CH_2-CH_2-COOCH_3$ | — | 139–41 |
| 58) | $-N_3$ | $-O-CO-CH_2-CH_3$ | — | 210–12 |

*Dextro configuration at the marked optically active centre.

The compounds in Table 2 were obtained from 1-acetyl-3,4-epoxy-4-phenylpiperidine (Example 20) and are all of formula III above wherein $R_1$ is $-COCH_3$ and $R_4$ is hydrogen.

Table 2

| Example | $R_2$ | $R_3$ | M.P. (° C) Base | M.P. (° C) HCl Salt |
|---|---|---|---|---|
| 59) | $-NH-CH_3$ | —OH | — | 243–5 |
| 60) | —OH | $-N(CH_2CH_2)_2O$ (morpholino) | 163–6 | — |

Table 2-continued

| Example | R₂ | R₃ | M.P. (°C) Base | HCl Salt |
|---|---|---|---|---|
| 61) | —OH | 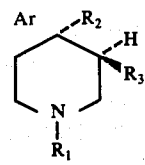 | 147–50 | — |

The compounds in Table 3 were obtained from 1-methyl-4-p-tolyl-3,4-epoxypiperidine and are all of formula III above wherein $R_1$ is methyl and $R_4$ is paramethyl.

| Example | R₂ | R₃ | M.P. of Base HCl Salt |
|---|---|---|---|
| 62) | OH | 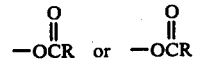 | 189–91° C |
| 63) | OH | —N(CH₃)(CH₃) | 249–50° C |
| 64) | OC—CH₃ (‖ O) | —N(CH₃)(CH₃) | 165–6° C |
| 65) | OH | —NH₂ | 140–1° C |

Other 4-arylpiperidine derivatives according to the present invention are as follows:

1-hydroxyethyl-3-dimethylamino-4-propoxy-4-parachlorophenylpiperidine;
3-(1-pyrrolidinyl)-4-acetoxy-4-phenylpiperidine; ethyl-[3-(4'morpholino)-4-hydroxy-4-paramethoxyphenyl-1-piperidyl]acetate;
2-[3'-(1''pyrrolidinyl)-4'-acetoxy-40'-phenyl-1-piperidyl]propionic acid;
1-(3'-hydroxy-3'-phenyl-propyl)-3-(1'-pyrrolidinyl)-4-acetoxy-4-phenylpiperidine;
1-(3-p-fluorobenzoylpropyl)-3-dimethylamino-4-hydroxy-4-phenylpiperidine;
1-dimethylaminoethyl-3-(1-piperidyl)-4-hydroxy-4-phenylpiperidine;
3-hydroxy-4-dimethylamino-4-(3'trifluoromethylphenyl)-piperidine;
1-benzoylmethyl-3-dimethylamino-4-hydroxy-4-(3',4',5'-trimethoxyphenyl)piperidine;
1-acetoxy-3-(1-pyrrolidinyl)-4-acetoxy-4-(m-trifluoromethyl-phenyl)piperidine;
1-(2'-hydroxy-2'-phenyl-ethyl)-3-dimethylamino-4-hydroxy-4-phenylpiperidine;
1-(3-p-fluorobenzoylpropyl)-3-dimethylamino-4-hydroxy-4-(m-methoxy-phenyl)piperidine;
3-dimethylamino-4-acetoxy-4-(2'-napthyl)piperidine;
1n-butyl-3-dimethylamino-4-acetoxy-4-phenylpiperidine;
1-methyl-3-(1-pyrrolidinyl)-4-methoxy-4-phenylpiperidine.

What is claimed is:

1. A 4-arylpiperidine derivative of the formula I:

$$\text{Ar} \underset{R_1}{\overset{R_2}{\underset{N}{\bigcirc}}} \overset{H}{R_3} \qquad I$$

wherein $R_1$ is hydrogen, lower alkyl, phenyl or phenyl lower alkyl; one of $R_2$ and $R_3$ represents morpholino, and the other of $R_2$ and $R_3$ represents hydroxyl, $$-\underset{\underset{O}{\|}}{O}CR \quad \text{or} \quad -\underset{\underset{O}{\|}}{O}CR$$

wherein R is lower alkyl; and Ar represents phenyl or naphthyl; or a pharmaceutically acceptable addition salt thereof with an organic acid or inorganic acid.

2. A compound according to claim 1 which is 1-methyl-4-phenyl-4-hydroxy-3-(4-morpholinyl)piperidine; or a pharmaceutically acceptable acid addition salt thereof with an organic acid or inorganic acid.

3. A compound according to claim 1 which is 1-methyl-4-phenyl-4-propionyloxy-3-(4-morpholinyl)piperidine; or a pharmaceutically acceptable acid addition salt thereof with an organic acid or inorganic acid.

4. An antidepressant pharmaceutical composition comprising an effective amount of said 4-arylpiperidine derivative of claim 1, as the active antidepressant ingredient, in combination with a pharmaceutically acceptable carrier or diluent thereof.

* * * * *